United States Patent [19]

Duggan

[11] Patent Number: 4,622,408

[45] Date of Patent: Nov. 11, 1986

[54] VINYL PHENYLTHIOCARBONATE

[75] Inventor: Angelina J. Duggan, Lawrenceville, N.J.

[73] Assignee: Merck & Co., Inc., Rahway, N.J.

[21] Appl. No.: 313,921

[22] Filed: Oct. 22, 1981

Related U.S. Application Data

[60] Continuation of Ser. No. 139,323, Apr. 11, 1980, abandoned, which is a division of Ser. No. 18,956, Mar. 9, 1979, abandoned, which is a division of Ser. No. 948,717, Oct. 5, 1978, abandoned.

[51] Int. Cl.$^4$ .................. C07C 125/06; C07C 101/02; C07D 207/00; C07D 209/20
[52] U.S. Cl. .................................... 548/533; 548/496; 548/341; 560/157; 560/24; 560/155; 560/115; 558/248; 560/160; 560/165
[58] Field of Search ............. 260/455 B; 560/24, 155, 560/115, 157; 558/248; 548/533, 496

[56] References Cited

U.S. PATENT DOCUMENTS 3,095,408  6/1963  Anderson et al. .................... 560/24
3,711,458  1/1973  Olofson et al. ....................... 560/24

OTHER PUBLICATIONS

Fieser and Fieser, *Advanced Organic Chemistry*, (1961) pp. 1014–1019.
Olofson et al., *Journal of Organic Chemistry*, 45, 2538–2541 (1980).

*Primary Examiner*—Henry R. Jiles
*Assistant Examiner*—Robert C. Whittenbaugh
*Attorney, Agent, or Firm*—David L. Rose

[57] ABSTRACT

The novel reagent, vinyl phenylthiocarbonate, is prepared. It is useful for the introduction of the vinyloxycarbonyl protecting group which is a valuable protecting group for amines, amino acids, peptides, proteins and phenols.

1 Claim, No Drawings

VINYL PHENYLTHIOCARBONATE

This is a continuation of application Ser. No. 139,323, filed 4/11/80, abandoned, which is a divisional of Ser. No. 18,956 filed 3/9/79, now abandoned, which in turn is a divisional of Ser. No. 948,717 filed 10/5/78, now abandoned.

BACKGROUND OF THE INVENTION

The vinyloxycarbonyl unit is a useful moiety for the N-protection of amino acids, and in the protection of phenols. However, its introduction via vinyl chloroformate suffers from the difficulty in preparing pure vinyl chloroformate from either the gas phase decomposition of ethylene glycol bis(chloroformate) or by acylation of ketone enolates with phosgene. The present invention is directed to the synthesis of vinyl phenylthiocarbonate, hereinafter also referred to as VOC-SPh, and to the use of VOC-SPh for the introduction of the vinyloxycarbonyl protective group, hereinafter also referred to as VOC, into amino acids.

The lithium enolate of acetaldehyde (III) is formed by the action of n-butyllithium (II) on tetrahydrofuran (I) with ethylene and butane generated as by-products according to the following scheme:

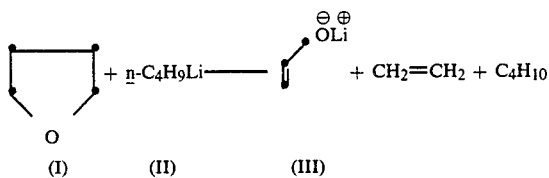

According to the present invention, acylation with phenyl thiochloroformate (IV) affords vinyl phenylthiocarbonate (V) in 65% isolated yield according to the following scheme:

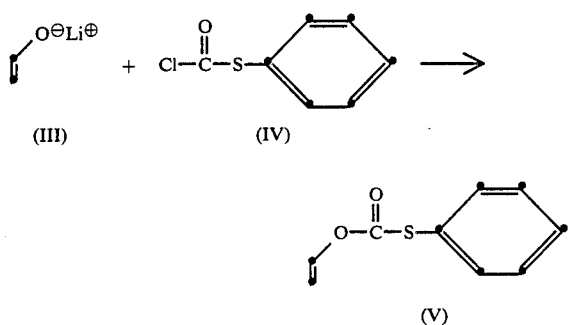

In contrast to vinyl chloroformate, vinyl phenylthiocarbonate is very stable towards light and ambient temperatures with no decomposition observed by NMR after one week in deuterochloroform solution. Although the reagent is stable to aqueous base, it reacts readily with amino acids at about pH 9.5 to generate the vinyl urethane, i.e., vinyloxycarbonyl amino acid, hereinafter also referred to as VOC-AA, and thiophenol according to the following scheme:

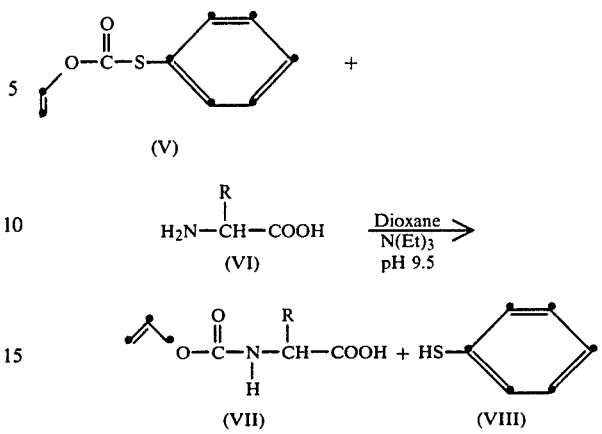

wherein R is the amino acid side chain.

The reaction proceeds most efficiently in solvent systems, such as dioxane-water or DMF-water, which afford the proper polarity for concurrent solubility of the VOC-SPh and the amino acid and weak bases such as triethylamine.

The following Examples are given for the purpose of illustration and not by way of limitation.

EXAMPLE 1

Preparation of Vinyl Phenylthiocarbonate

Tetrahydrofuran, 90 ml. (1.11 moles), freshly distilled over $CaH_2$ was stirred and cooled to 0° C. under nitrogen in an ice bath. n-Butyl lithium, (0.099 moles) in 2.2 ml. hexane, was added dropwise at such a rate as to maintain 0°–10° C. temperature. The ice bath was removed after 10 minutes and the reaction was allowed to stir at ambient temperature for 17 hours. The reaction mixture was a pale yellow slightly turbid solution. The reaction was cooled to −78° C. in a dry ice-$CO_2$ bath and a few crystals of hydroquinone were added. The phenyl thiochloroformate was added quickly (maintaining temperature below −45° C., stirred at −78° C. for one-half hour and poured into 100 ml. of water. The organic layer was separated and the aqueous layer was extracted with ether 3×50 mls. The combined organic layers were dried with anhydrous sodium sulfate, filtered and concentrated in vacuo (bath temperature less than 30° C.) to yield a mobile yellow oil—14 g. (92%). The sample was dissolved in hexane and placed on 175 g. of silica gel. Elution with hexane yielded purified, 12 g. (68%), phenylthiocarbonate.

EXAMPLE 2

Preparation of Vinyl Phenylthiocarbonate n-Butyllithium (0.173 moles, 71 ml. of a 2.45M solution in hexane) was added rapidly at <35° C. to dry THF (130 ml.) maintained under $N_2$. The reaction was heated at 35° C. for 2 hours, cooled to room temperature for one hour and transferred rapidly via a cannulae to 28.5 g. (0.165 moles) of phenyl thiochloroformate in 80 ml. of THF (which contained a few crystals of hydroquinone) at −40° to −45° C. The reaction was stirred at −45° C. for 1 hour, quenched with 100 ml. of saturated NaCl solution and warmed to room temperature. The aqueous layer was extracted with 50 ml. of hexane and the combined organic layers were dried over anhydrous $Na_2SO_4$ and concentrated to afford 29.3 g. (98%) of a yellow oil. Distillation, b.p. 67°–69° C. (0.4 torr), afforded 19.3 g. (65%) of vinyl phenylthiocarbonate as a colorless oil: IR (CHCl$_3$) 3100, 2975, 1740, 1650 cm$^{-1}$; NMR (CDCl$_3$): δ4.65 (1H, d, d, J=4 and J=1 Hz), 4.85 (1H, d, d, J=7 and J=1 Hz), 7.25 (1H, d, d, J=7 and J=3 Hz), 7.67–7.40 (5H, m); MS 180, 109, 137, 43.

Anal. calc'd for C$_9$H$_8$O$_2$S: C, 59.98; H, 4.47; S, 17.79. Found: C, 59.39 H, 4.52; S, 17.79.

EXAMPLE 3

Preparation of Vinyloxycarbonylglycine

To a solution of 0.66 g. glycine dissolved in water was added 1.8 ml. triethylamine followed by 1.8 g. vinyl phenylthiocarbonate in 180 ml. dioxane. The reaction was stirred at ambient temperature for 16 hours and poured onto 50 ml. of water (odor of thiophenol evident). The pH of the solution was 10. The reaction was concentrated in an ice bath and the pH adjusted to 6 with 5N HCl and extracted with 4×25 ml. of hexane to remove the thiophenol. The aqueous layer was acidified to pH 2 and extracted 4x with methylene chloride. The methylene chloride was dried with Na$_2$SO$_4$, filtered and concentrated to yield 0.7 g. of crude product (60%) which yielded 300 mg. of crystalline product (25%) m.p. 94°–95° C. from methylene chloride-hexane.

EXAMPLE 4

Preparation of Vinyloxycarbonylglycine

Vinyl phenylthiocarbonate 4.43 g. (0.0246 moles) in 50 ml. dioxane, was added to 1.85 g. (0.0246 moles) of glycine in 40 ml. H$_2$O. The pH was maintained at 9.5 with N(Et)$_3$ for 16 hours at room temperature. The reaction was acidified to pH 5.8 with 5N HCl and extracted with 4×30 ml. of hexane to remove the thiophenol. The aqueous layer was acidified to pH 2, saturated with NaCl and stirred 15 minutes with 3×50 ml. of EtOAc. The combined EtOAc extracts were dried over anhydrous NA$_2$SO$_4$ and concentrated to afford 2.89 g. (78%) of the VOC-AA, m.p. 90°–91° C. R. A. Olofson et al., *Tetrahedron Lett.*, 1563 (1977). Recrystallization from CH$_2$Cl$_2$-hexane afforded crystals, m.p. 94°–96° C.: IR (CHCl$_3$): 3500, 3400, 2975, 1750, 1700, 1575, 1550 cm$^{-1}$; NMR (d$_6$DMSO): δ3.65 (2H, d, J=3 Hz), 4.45 (1H, d, d, J=3 and J=1 Hz), 4.75 (1H, d, d, J=7 and J=1 Hz), 7.08 (1H, d, d, J=7 and J=3 Hz); CIMS: 203 (M+1), 159, 128.

Anal. calc'd. for C$_5$H$_7$O$_4$N: C, 41.38; H, 4.88; N, 9.65. Found: C, 41.56; H, 4.94; N, 9.33.

The following VOC-AA set forth in Table I were prepared by the method of Example 4.

TABLE I

Preparation of VOC AA from Vinyl Phenylthiocarbonate

| Amino Acid | Product | Yield[a,b] |
|---|---|---|
| Glycine | VOC—glycine | 80% |
| L-Phenylalanine | VOC—Phenylalanine | 60% |
| L-Proline | VOC—Proline | 77% |
| Glycylglycine | VOC—glycylglycine | 50% |

[a]Each product was one spot on TLC and had IR, NMR and MS data in accordance with the proposed structure.
[b]The reaction was performed in 2:1 dioxane-water, maintained at pH 9.5 with N(Et)$_3$.

Any departure from the above description which conforms to the present invention is intended to be included within the scope of the claims.

What is claimed is:

1. The process for preparing an N-protected amino acid

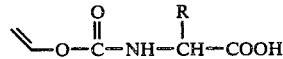

wherein R is the amino acid side chain which comprises reacting said amino acid

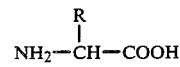

with vinyl phenylthiocarbonate

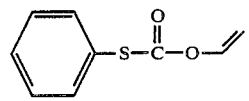

at a pH of 9.5 in a mixed solvent system of dioxane or DMF in water with a weak base.

* * * * *